United States Patent [19]

Nelson

[11] 4,110,383

[45] Aug. 29, 1978

[54] 2-DECARBOXY-2-HYDROXYMETHYL-3-7-INTER-M-PHENYLENE-ω-PHENYL-PGA$_1$ OR 9-DEOXY-9,10-DIDEHYDRO-PGD$_1$ COMPOUNDS

[75] Inventor: Norman A. Nelson, Galesburg, Mich.

[73] Assignee: The Upjohn Company, Kalamazoo, Mich.

[21] Appl. No.: 822,038

[22] Filed: Aug. 5, 1977

Related U.S. Application Data

[62] Division of Ser. No. 647,357, Jan. 8, 1976, Pat. No. 4,055,602.

[51] Int. Cl.$^2$ .................. C07C 49/82; C07C 49/84
[52] U.S. Cl. .................................. 260/590 C
[58] Field of Search ............... 260/590 C; 560/121

*Primary Examiner*—James O. Thomas, Jr.
*Assistant Examiner*—James H. Reamer
*Attorney, Agent, or Firm*—Robert A. Armitage

[57] ABSTRACT

This invention comprises certain analogs of the prostaglandins in which the C-1 carboxyl is replaced by a primary alcohol. Also provided in this invention, are novel chemical processes useful in the preparation of the above prostaglandin analogs. These prostaglandin analogs exhibit prostaglandin-like activity, and are accordingly useful for the same pharmacological purposes as the prostaglandins. Among these purposes are blood pressure lowering, labor induction at term, reproductive-cycle regulation, gastric antisecretory action, and the like.

39 Claims, No Drawings

2-DECARBOXY-2-HYDROXYMETHYL-3-7-INTER-M-PHENYLENE-ω-PHENYL-PGA₁ OR 9-DEOXY-9,10-DIDEHYDRO-PGD₁ COMPOUNDS

The present application is a divisional application of Ser. No. 647,357, filed Jan. 8, 1976, now issued as U.S. Pat. No. 4,055,602.

The present invention relates to prostaglandin analogs, for which the essential material constituting disclosure therefor is incorporated by reference here from U.S. Pat. No. 4,055,602, issued Oct. 25, 1977.

I claim:

1. A prostaglandin analog of the formula

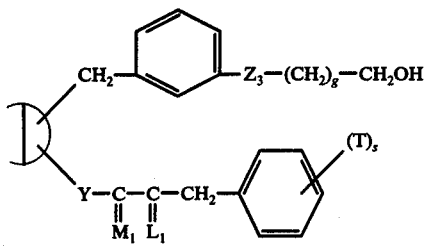

wherein $Z_3$ is oxa or methylene;
wherein D is

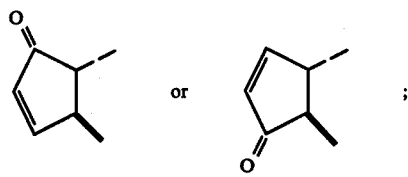

wherein Y is trans—CH=CH—;
wherein $M_1$ is

wherein $R_5$ is hydrogen or methyl;
wherein $L_1$ is

or a mixture of

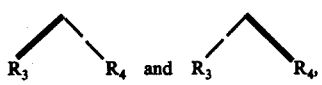

wherein $R_3$ and $R_4$ are hydrogen, methyl, or fluoro, being the same or different, with the proviso that one of $R_3$ and $R_4$ is methyl only when the other is hydrogen or methyl;
wherein $g$ is one, 2, or 3; and
wherein $s$ is zero, one, 2, or 3 and T is chloro, fluoro, trifluoromethyl, alkyl of one to 3 carbon atoms, inclusive, or alkoxy of one to 3 carbon atoms, inclusive, the various T's being the same or different, with the proviso that not more than two T's are other than alkyl.

2. A compound according to claim 1, wherein D is

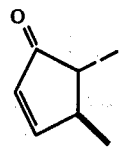

3. A compound according to claim 2, wherein s is zero or one and T is chloro, fluoro, or trifluoromethyl.
4. A compound according to claim 3, wherein at least one of $R_3$ and $R_4$ is fluoro.
5. A compound according to claim 4, wherein $R_3$ and $R_4$ are both fluoro.
6. A compound according to claim 5, wherein $R_5$ is methyl.
7. 2-Decarboxy-2-hydroxymethyl-15-methyl-16,16-difluoro-17-phenyl-3,7-inter-m-phenylene-3-oxa-4,5,6,18,19,20-PGA₁, a compound according to claim 6.
8. A compound according to claim 5, wherein $R_5$ is hydrogen.
9. 2-Decarboxy-2-hydroxymethyl-16,16-difluoro-17-phenyl-3,7-inter-m-phenylene-3-oxa-4,5,6,18,19,20-hexanor-PGA₁, a compound according to claim 8.
10. A compound according to claim 3, wherein at least one of $R_3$ and $R_4$ is methyl.
11. A compound according to claim 10, wherein $R_3$ and $R_4$ are both methyl.
12. A compound according to claim 11, wherein $R_5$ is methyl.
13. 2-Decarboxy-2-hydroxymethyl-15,16,16-trimethyl-17-phenyl-3,7-inter-m-phenylene-3-oxa-4,5,6,18,19,20-hexanor-PGA₁, a compound according to claim 12.
14. A compound according to claim 11, wherein $R_5$ is hydrogen.
15. 2-Decarboxy-2-hydroxymethyl-16,16-dimethyl-17-phenyl-3,7-inter-m-phenylene-3-oxa-4,5,6,18,19,20-hexanor-PGA₁, a compound according to claim 14.
16. A compound according to claim 3, wherein $R_3$ and $R_4$ are both hydrogen.
17. A compound according to claim 16, wherein $R_5$ is methyl.
18. 2-Decarboxy-2-hydroxymethyl-15-methyl-17-phenyl-3,7-inter-m-phenylene-3-oxa-4,5,6,18,19,20-hexanor-PGA₁, a compound according to claim 17.
19. A compound according to claim 16, wherein $R_5$ is hydrogen.
20. 2-Decarboxy-2-hydroxymethyl-17-phenyl-3,7-inter-m-phenylene-3-oxa-4,5,6,18,19,20-hexanor-PGA₁, a compound according to claim 19.
21. A compound according to claim 20, wherein D is

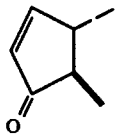

22. A compound according to claim 21, wherein s is zero or one and T is chloro, fluoro, or trifluoromethyl.
23. A compound according to claim 22, wherein at least one of $R_3$ and $R_4$ is fluoro.

24. A compound according to claim 23, wherein $R_3$ and $R_4$ are both fluoro.

25. A compound according to claim 24, wherein $R_5$ is methyl.

26. 2-Decarboxy-2-hydroxymethyl-16,16-difluoro-17-difluoro-17-phenyl-3,7-inter-m-phenylene-3-oxa-4,5,6,18,19,20-9-deoxy-9,10-didehydro-PGD$_1$, a compound according to claim 25.

27. A compound according to claim 24, wherein $R_5$ is hydrogen.

28. 2-Decarboxy-2-hydroxymethyl-16,16-difluoro-17-phenyl-3,7-inter-m-phenylene-3-oxa-4,5,6,18,19,20-hexanor-9-deoxy-9,10-didehydro-PGD$_1$, a compound according to claim 27.

29. A compound according to claim 22, wherein at least one of $R_3$ and $R_4$ is methyl.

30. A compound according to claim 29, wherein $R_3$ and $R_4$ are both methyl.

31. A compound according to claim 30, wherein $R_5$ is methyl.

32. 2-Decarboxy-2-hydroxymethyl-15,16,16-trimethyl-17-phenyl-3,7-inter-m-phenylene-3-oxa-4,5,6,18,19,20-hexanor-9-deoxy-9,10-didehydro-PGD$_1$, a compound according to claim 31.

33. A compound according to claim 30, wherein $R_5$ is hydrogen.

34. 2-Decarboxy-2-hydroxymethyl-16,16-dimethyl-17-phenyl-3,7-inter-m-phenylene-3-oxa-4,5,6,18,19,20-hexanor-9-deoxy-9,10-didehydro-PGD$_1$, a compound according to claim 33.

35. A compound according to claim 22, wherein $R_3$ and $R_4$ are both hydrogen.

36. A compound according to claim 35, wherein $R_5$ is methyl.

37. 2-Decarboxy-2-hydroxymethyl-15-methyl-17-phenyl-3,7-inter-m-phenylene-3-oxa-4,5,6,18,19,20-hexanor-9-deoxy-9,10-didehydro-PGD$_1$, a compound according to claim 36.

38. A compound according to claim 35, wherein $R_5$ is hydrogen.

39. 2-Decarboxy-2-hydroxymethyl-17-phenyl-3,7-inter-m-phenylene-3-oxa-4,5,6,18,19,20-hexanor-9-deoxy-9,10-didehydro-PGD$_1$, a compound according to claim 38.

* * * * *

UNITED STATES PATENT OFFICE
CERTIFICATE OF CORRECTION

Patent No. 4,110,383    Dated August 29, 1978

Inventor(s) Norman A. Nelson

It is certified that error appears in the above-identified patent and that said Letters Patent are hereby corrected as shown below:

Column 3, line 6, "17-difluoro-17-phenyl-" should read -- 17-phenyl- --; line 7, "4,5,6,18,19,20-9-deoxy" should read -- 4,5,6,18,19,20-hexanor-9-deoxy --.

Signed and Sealed this

Eighteenth Day of September 1979

[SEAL]

Attest:

LUTRELLE F. PARKER
Attesting Officer    Acting Commissioner of Patents and Trademarks